(12) United States Patent
Hirota et al.

(10) Patent No.: US 7,165,701 B2
(45) Date of Patent: Jan. 23, 2007

(54) DROPLET NOZZLE FOR USE IN EYE DROP CONTAINER

(75) Inventors: Koji Hirota, Kanazawa (JP); Masaki Hayakawa, Kanazawa (JP)

(73) Assignee: Shinko Chemical Co., Ltd., Ishikawa (JP)

( * ) Notice: Subject to any disclaimer, the term of this patent is extended or adjusted under 35 U.S.C. 154(b) by 172 days.

(21) Appl. No.: 10/933,057

(22) Filed: Sep. 2, 2004

(65) Prior Publication Data
US 2005/0087572 A1  Apr. 28, 2005

(30) Foreign Application Priority Data
Sep. 26, 2003 (JP) ............................ 2003-335063
Jun. 3, 2004 (JP) ............................ 2004-165290

(51) Int. Cl.
B65D 37/00 (2006.01)
B65D 47/18 (2006.01)

(52) U.S. Cl. ........................ 222/212; 222/420; 222/421

(58) Field of Classification Search ................ 222/212, 222/420, 421, 422
See application file for complete search history.

(56) References Cited

U.S. PATENT DOCUMENTS

| | | | |
|---|---|---|---|
| 2,576,403 A * | 11/1951 | Kirschenbaum | ............ 222/421 |
| 4,568,004 A | 2/1986 | Goncalves | |
| 5,431,314 A * | 7/1995 | Bonnelye et al. | ............ 222/420 |
| 5,464,122 A | 11/1995 | Lishfey | |
| 6,197,008 B1 * | 3/2001 | Hagele | ......................... 604/295 |
| 2004/0079766 A1* | 4/2004 | Kokubo | ......................... 222/212 |
| 2005/0173456 A1* | 8/2005 | Backes | ......................... 222/212 |

FOREIGN PATENT DOCUMENTS

| | | |
|---|---|---|
| DE | 295 11 594 | 9/1995 |
| JP | 11-128313 | 5/1999 |
| JP | 2002-308310 | 10/2002 |

* cited by examiner

Primary Examiner—Joseph A. Kaufman
(74) Attorney, Agent, or Firm—Jordan and Hamburg LLP

(57) ABSTRACT

A nozzle includes a top portion projecting in the same direction as an opening of a container, and a plurality of liquid-medicine passages formed at an outer periphery of the top portion. When the container is inclined, a liquid medicine in the container leaks out therefrom via orifices of the individual liquid-medicine passages communicated with the opening of the container, so as to form a droplet on an outside surface of the top portion, whereby the liquid medicine is applied in a droplet.

4 Claims, 11 Drawing Sheets

DROPLET NOZZLE FOR USE IN EYE DROP CONTAINER

CROSS REFERENCE TO RELATED APPLICATION

The disclosure of Japanese Patent Applications No. 2003-335063 filed Sep. 26, 2003 and No. 2004-165290 filed Jun. 3, 2004 each of which includes specification, drawings and claims is incorporated herein by reference in its entirety.

BACKGROUND OF THE INVENTION

1. Field of the Invention

The present invention relates to a droplet nozzle for use in eye drop container, which is capable of accurately applying a liquid medicine in a droplet in the eye when the container is inclined at any angle.

2. Description of the Related Art

There is known an eye drop container capable of applying a liquid medicine in the eye accurately in a substantially constant quantity not only when the container is directed downward but also when the container is inclined at any angle (Japanese Unexamined Patent Publication No. 11-128313).

A specific inner plug is fitted in an opening of this eye drop container. The inner plug has a dome-shaped head portion which is elastically supported by a plurality of tongues at an end of a cylindrical main body which is fitted in the opening of the container. When the container is inclined, the inner plug is capable of forming a fixed quantity of droplet by guiding a liquid medicine in the container to an outside surface of the head portion via gaps between the main body and the head portion. Therefore, the container is allowed to apply the liquid medicine in the eye accurately as a substantially fixed quantity of droplet.

According to such a prior art, the liquid medicine guided from the container adheres to the outside surface of the head portion and forms a droplet thereon. However, the droplet is prone to flow down on the outside surface of the main body when the container is returned to an upright position, because a diameter of the head portion is substantially equal to an outside diameter of the main body. Accordingly, a so-called fluid run is not infrequently encountered.

SUMMARY OF THE INVENTION

It is therefore an object of the invention to address the aforementioned problem of the prior art and to provide a droplet nozzle for use in eye drop container in which a plurality of liquid-medicine passages are formed in an outer periphery of a dome-shaped top portion, thereby preventing the occurrence of the fluid run and attaining the ability to apply the liquid medicine in the eye accurately in a droplet when the container is inclined at any angle.

According to an aspect of this invention, there is provided a droplet nozzle for use in eye drop container, wherein a plurality of liquid-medicine passages are formed at an outer periphery of a top portion in a direction of an axis of the top portion shaped like a dome and projecting in the same direction as an opening of a container, and the plurality of liquid-medicine passages are communicated with the opening of the container via respective orifices thereof opening at places closest to the axis of the top portion.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

Preferred embodiments of the invention will hereinbelow be described with reference to the accompanying drawings.

First Preferred Embodiment

Figure 1B:
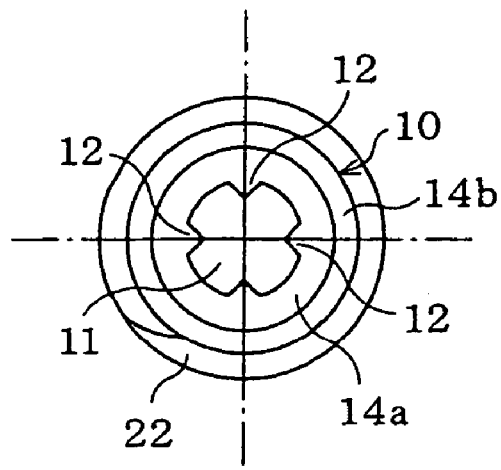
FIG. 1B is a top plan view of the nozzle.
Figure 1A:
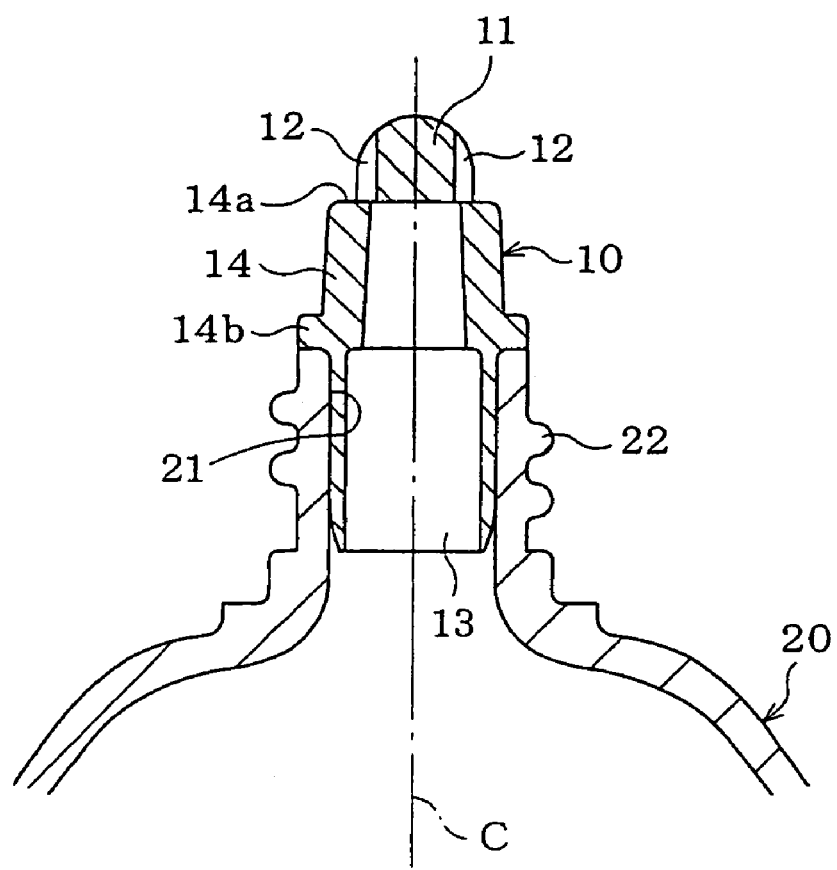
FIG. 1A is a vertical sectional view of a nozzle of a first embodiment.

A droplet nozzle for use in eye drop container includes a dome-shaped top portion 11 and a plurality of liquid-medicine passages 12, 12 . . . formed at an outer periphery of the top portion 11 (FIGS. 1A and 1B). FIGS. 1A and 1B are a central vertical sectional view and a top plan view of the nozzle, respectively. The illustrated top portion 11 forms an inner plug 10 with a skirt 13 pressed into an opening 21 of the container 20, the inner plug 10 being separate from the container 20.

An intermediate portion 14 shaped like a thick cylinder is formed at the foot of the top portion 11 via a step 14a for common draining. An outer flange 14b is formed at a lower end of the intermediate portion 14, the outer flange 14b conforming to an end face of the opening 21 of the container 20. Furthermore, the thin skirt 13 extends vertically downwardly from the lower end of the intermediate portion 14. The top portion 11, the intermediate portion 14 and the skirt 13 are formed on the same axis C and hence, the top portion 11 projects in the same direction as the opening 21 of the container 20. The maximum outside diameter of a lower end of the top portion 11 is smaller than an outside diameter of the intermediate portion 14, so that the step 14a projects outwardly from the outer periphery of the top portion 11.

Figure 2:
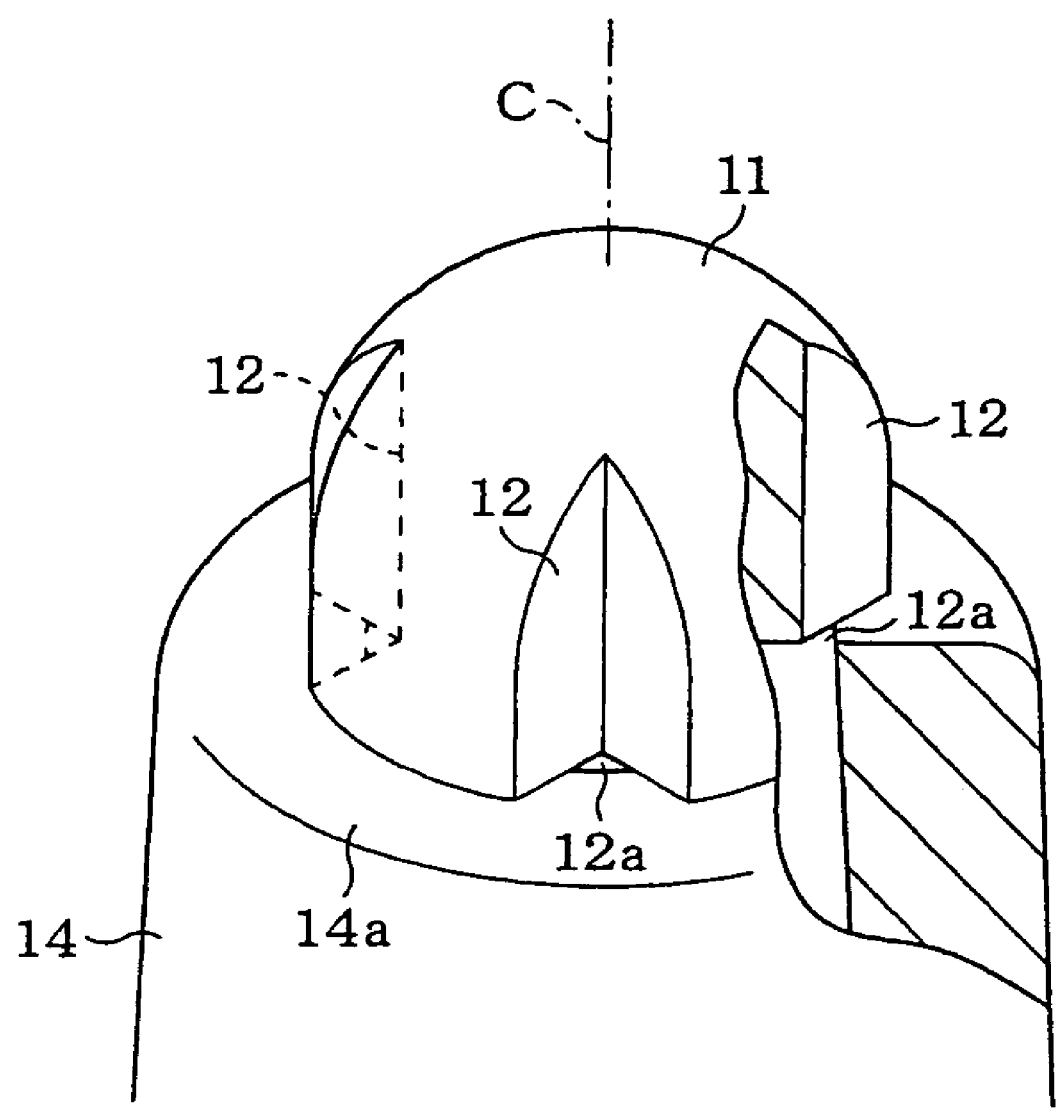
FIG. 2 is an expanded perspective view of the nozzle of substantial part.

The individual liquid-medicine passages 12 are formed in the direction of the axis C of the top portion 11 and arranged around the top portion 11 with equal spacing (FIGS. 1A, 1B and 2). Each of the liquid-medicine passages 12 is formed V-shaped in section opening in a radial direction of the top portion 11. A lower end of each of the liquid-medicine passages 12 is communicated with an interior of the intermediate portion 14 or the opening 21 of the container 20 via an orifice 12a opening at place closest to the axis C of the top portion 11 in the same direction as the axis C. A ridge line at the deepest part of each liquid medicine passage 12 is located nearer to the axis C than an inside surface of the intermediate portion 14, so that the orifice 12a opens in the form of an angular sector at the lower end of each liquid medicine passage 12. Each of the liquid-medicine passages 12 is formed to have such a sectional area as to be readily filled with the liquid medicine due to the surface tension of the liquid medicine.

Figure 3:
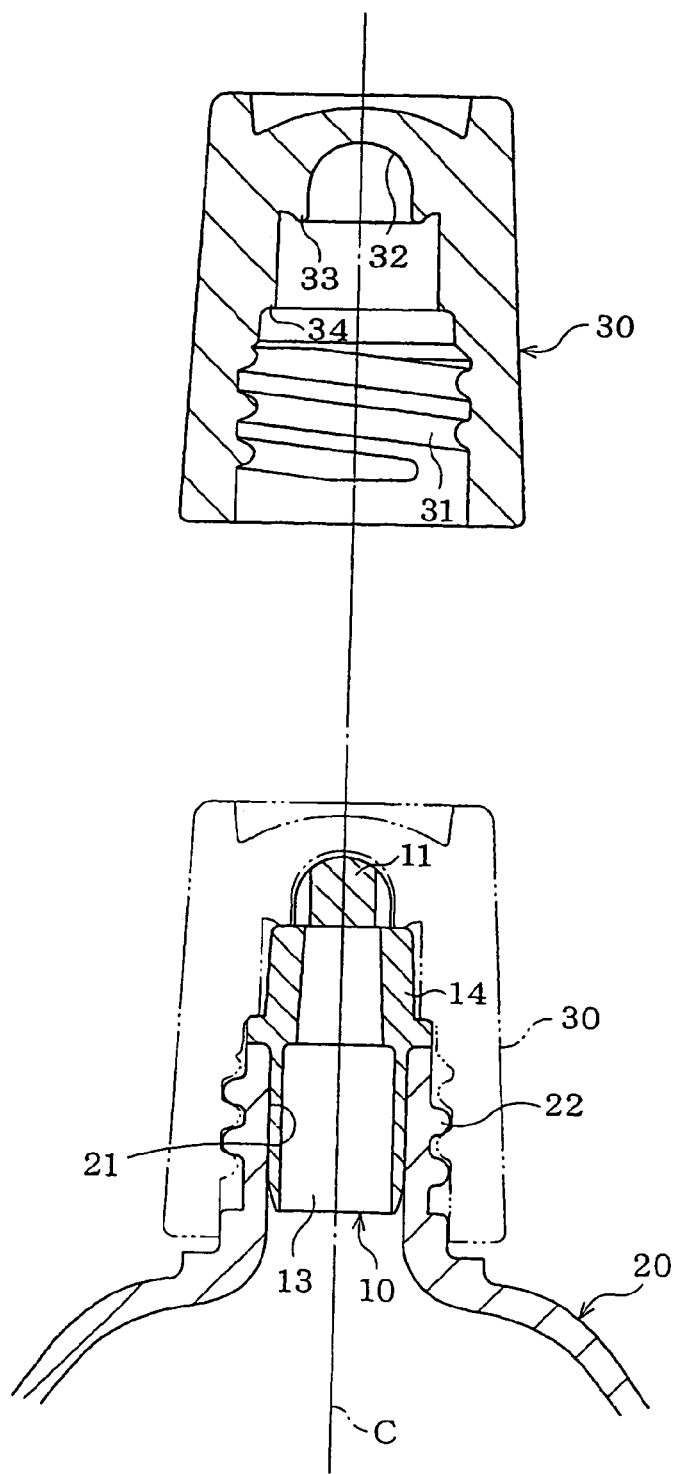
FIG. 3 is a vertical sectional view of a cap and the nozzle.

A male screw 22 for a cap 30 is formed in the opening 21 of the container 20 (FIGS. 1A, 1B and 3). In the cap 30, a female screw 31 matching with the male screw 22, a storage space 32 shaped like a dome opening downward for storing the top portion 11 of the inner plug 10, a sealing portion 33 corresponding to the step 14a of the inner plug 10, and a stopper 34 corresponding to the outer flange 14b and serving to prevent over-tightening of the cap 30 (depicted by the solid line in FIG. 3). The cap 30 may be tightened down on the opening 21 of the container 20, thereby releasably sealing the opening 21 via the inner plug 10 (depicted by the dash-double-dot line in FIG. 3). In a case where the container 20 and the cap 30 are each made of a hard material in a single piece, a soft material suited to the hard materials is selected for forming the inner plug 10.

In a case where the container 20 is made of a hard material such as polyethylene terephthalate, or polyethylene naphthalate, for example, a soft material such as low-density polyethylene, polypropylene or polymethyl pentene may be used for forming the inner plug 10 so that the cap 30 made of a hard material such as ABS (acrylonitrile-butadiene-styrene) resin or AS (acrylonitrile-styrene) resin may readily achieve good sealing performance.

When the container 20 with the cap 30 removed therefrom is directed downward (FIG. 4A), a liquid medicine W in the container 20 leaks into the liquid-medicine passages 12 via the orifices 12a, 12a, . . . of the inner plug 10 (in a direction of the arrow in the figure), fills up the liquid-medicine passages 12, 12 . . . and then, forms a droplet W1 at the lowest point of an end of the top portion 11. The liquid medicine W is applied as a droplet W1 at a time. It is thus ensured that the liquid medicine is applied in the eye accurately in a substantially fixed quantity each time. When, on the other hand, the container 20 is inclined at an angle (FIG. 4B), the liquid medicine W leaking into the liquid-medicine passages 12, 12 . . . (in a direction of the arrow in the figure) in a similar manner to the above forms a droplet W1 at the lowest point of the top portion 11. Thus, the liquid medicine W may be applied in the eye as a droplet W1 each time. When the liquid medicine W is applied in a droplet in the eye, a body of the container 20 may be elastically deformed by properly pressing down on the body, thereby forcing the liquid medicine W to flow out.

Figure 4A:
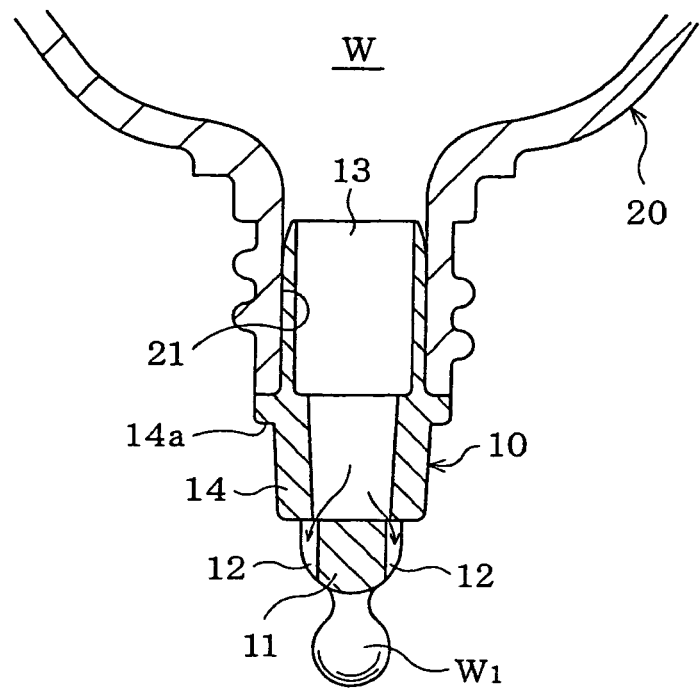
FIG. 4A is a vertical sectional view of a container directed downward.
Figure 4B:
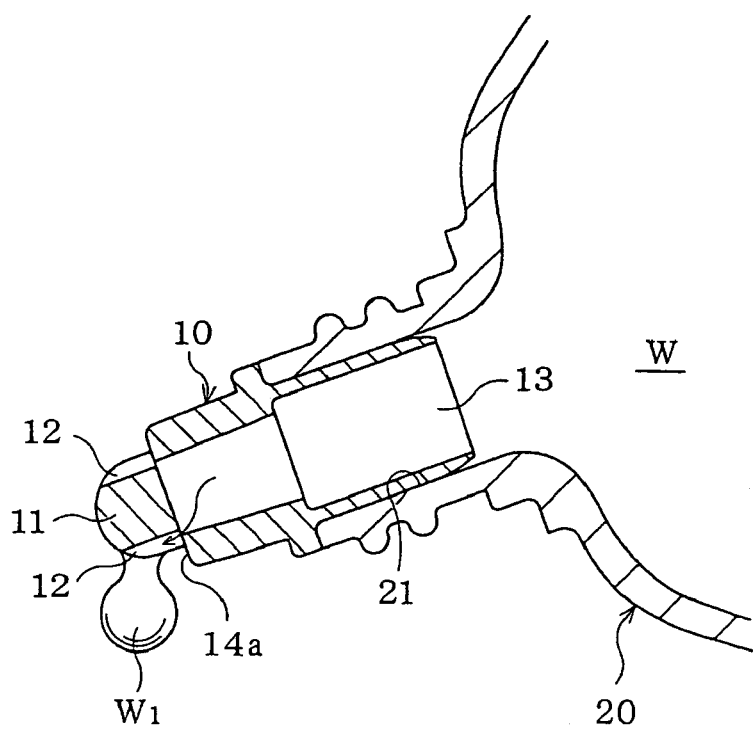
FIG. 4B is a vertical sectional view of the container inclined downward.

When the container 20 in the position shown in FIGS. 4A or 4B is returned to the upright position, the liquid medicine W adherent to the outside surface of the top portion 11 smoothly flows back into the container 20 via the orifices 12a, 12a . . . . This is because the step 14a for draining is formed at the foot of the top portion 11 and besides, the liquid medicine W appearing on the top portion 11 is mostly in the liquid-medicine passages 12, 12 . . . and the orifices 12a communicated with the opening 21 of the container 20 are opened at the respective lower ends of the liquid-medicine passages 12.

Second Preferred Embodiment

Figure 5B:
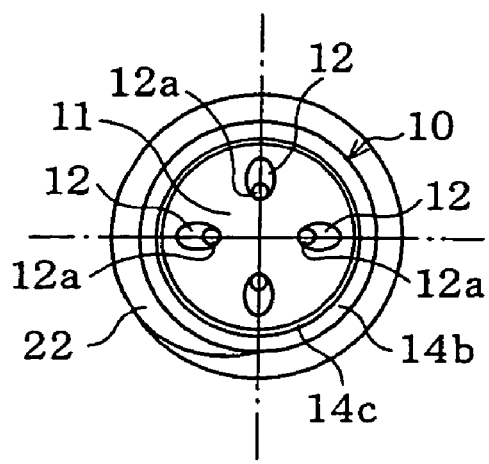
FIG. 5B is a top plan view of the nozzle of the second embodiment.
Figure 5A:
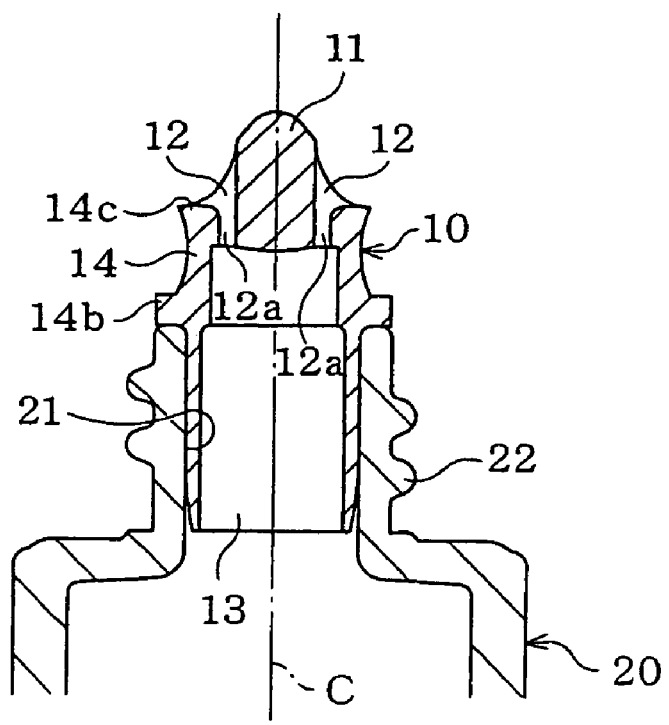
FIG. 5A is a vertical sectional view of a nozzle of a second embodiment.

The liquid-medicine passages 12, 12 . . . formed at the outer periphery of the top portion 11 may be formed oblong-shaped in section, a longitudinal axis of which extends radially of the top portion 11 (FIGS. 5A and 5B). It is noted that FIGS. 5A and 5B are a central vertical sectional view and a top plan view, respectively.

Formed at the foot of the top portion 11 is an edge 14c for common draining. The individual liquid-medicine passages 12 extending in the direction of the axis C of the top portion 11 are communicated with the opening 21 of the container 20 via the orifices 21a opening at places closest to the axis C in the same direction as the axis C. The orifices 12a are each formed as a through hole at the lower end of each corresponding liquid medicine passage 12 in parallel with the axis C.

Figure 6:
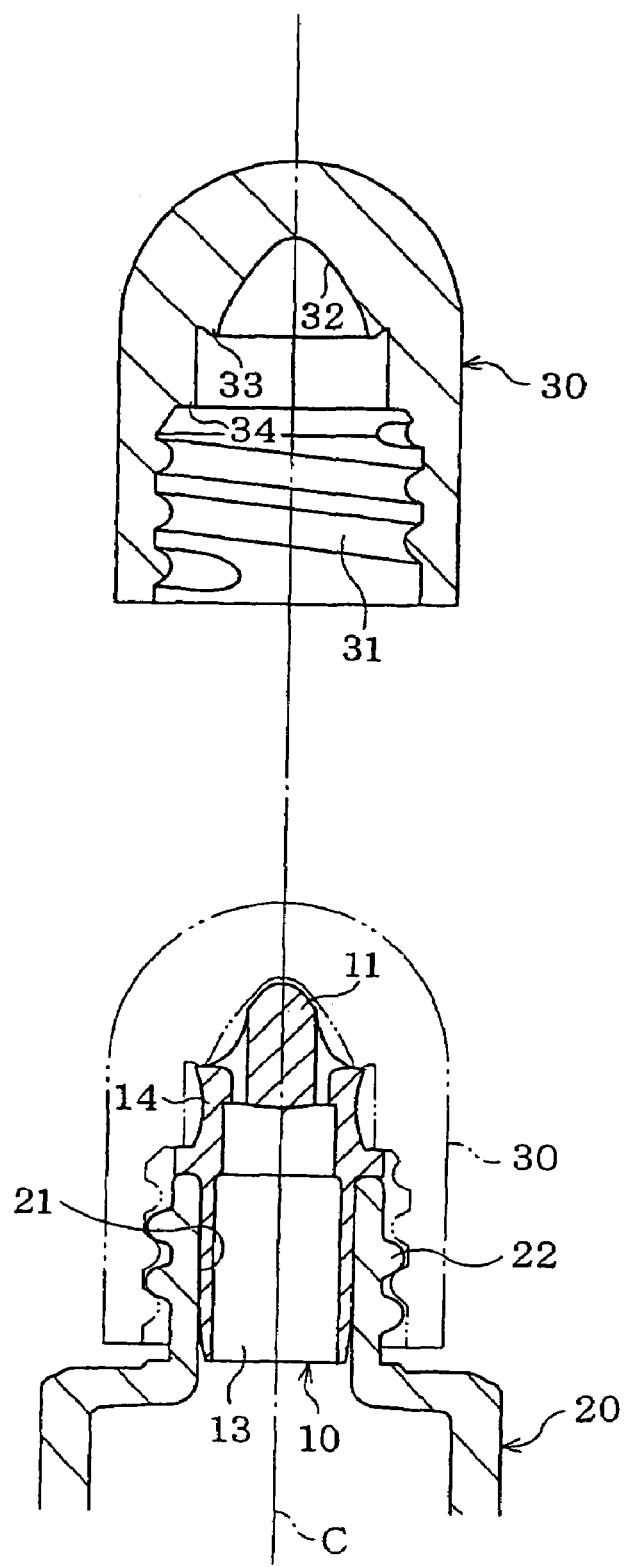
FIG. 6 is a vertical sectional view of a cap and the nozzle of the second embodiment.

In the cap 30 fitting with the inner plug 10 shown in FIGS. 5A and 5B, other than the female screw 31 matching with the male screw 22 on the container 20, the storage space 32 for storing the top portion 11, the sealing portion 33 corresponding to the edge 14c, and the stopper 34 corresponding to the outer flange 14b are formed (depicted by the solid line in FIG. 6). The cap 30 is engaged with the opening 21 via the female screw 31 and the male screw 22, thereby releasably sealing the opening 21 via the inner plug 10 (depicted by the dash-double-dot line in the figure).

Figure 7A:
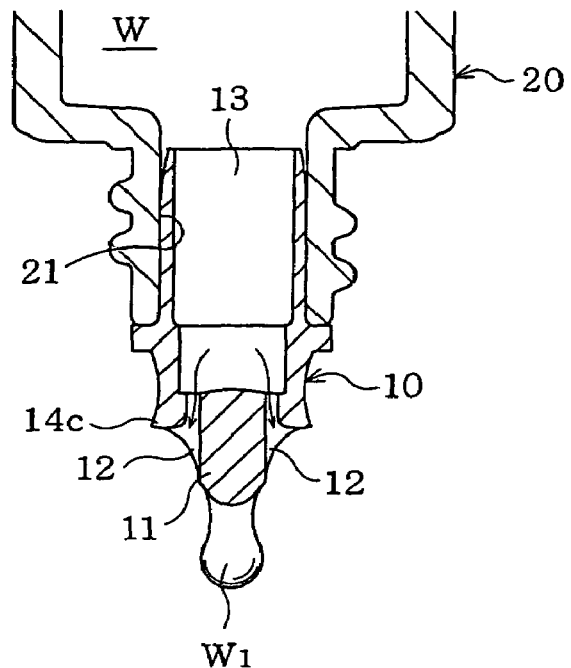
FIG. 7A is a vertical sectional view of a container directed downward.
Figure 7B:
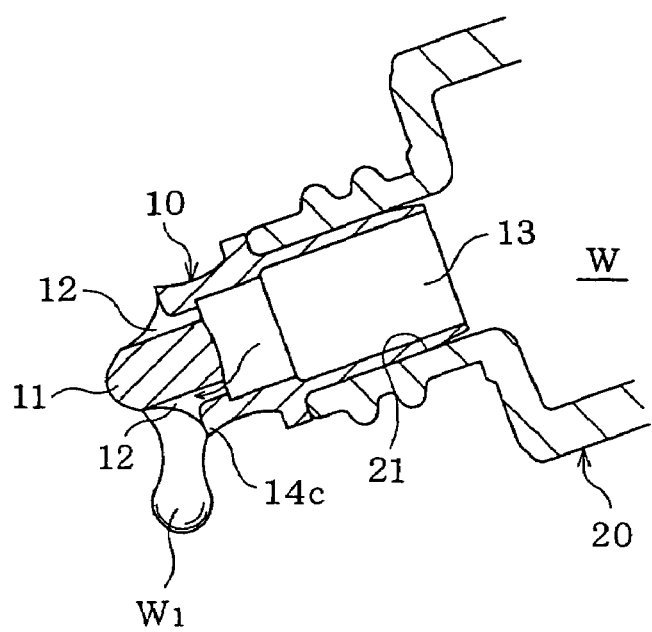
FIG. 7B is a vertical sectional view of the container inclined downward.

When the container 20 with the cap 30 removed therefrom is directed downward (FIG. 7A) or inclined downwardly (FIG. 7B), the liquid medicine W in the container 20 leaks into the liquid-medicine passages 12, 12 . . . via the orifices 12a, 12a . . . (in directions of the arrows shown in FIGS. 7A and 7B, respectively), so that the liquid medicine forms a droplet W1 on the outside surface of the top portion 11 such as to be applied in a droplet. When the container 20 is returned to the upright position, the liquid medicine W on the top portion 11 flows back into the container 20 via the orifices 12a, 12a . . . so that there occurs no fluid run. The edge 14c at the foot of the top portion 11 drains the liquid medicine W, thereby preventing the fluid run more effectively. Specifically, the nozzle is capable of accurately applying the liquid medicine W in a droplet without causing the fluid run, even when the container 20 shown in FIG. 7B is held in a manner that the opening 21 thereof is directed upward at an angle of about 5° relative to the horizontal direction.

Third Preferred Embodiment

Figure 8B:
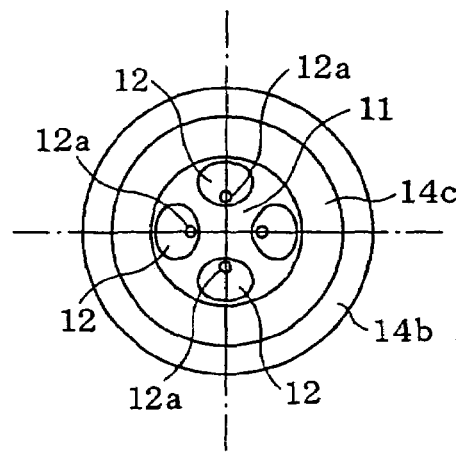
FIG. 8B is a top plan view of the nozzle of the third embodiment.
Figure 8C:
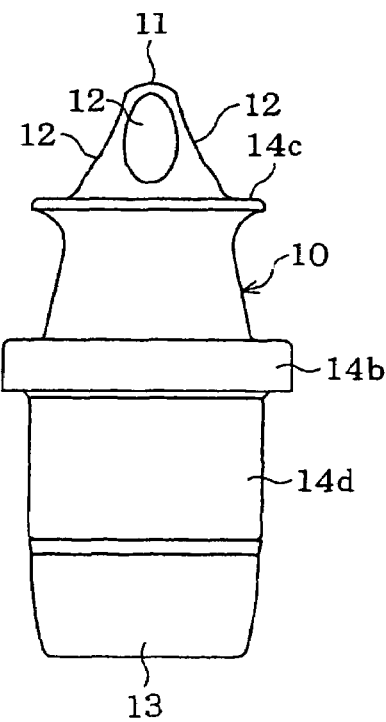
FIG. 8C is a front elevational view of the nozzle of the third embodiment.
Figure 8A:
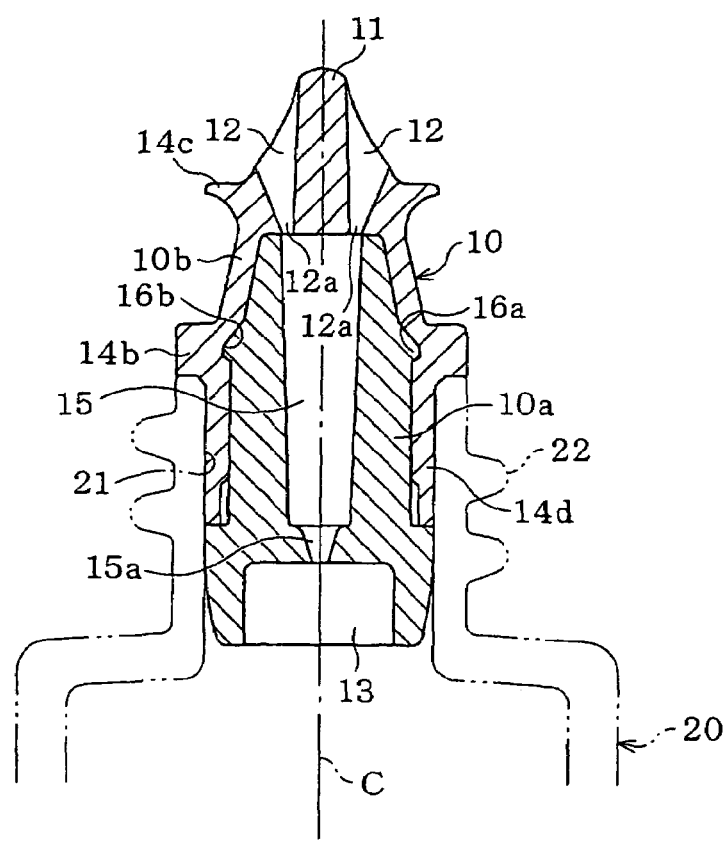
FIG. 8A is a vertical sectional view of a nozzle of a third embodiment.

The inner plug 10 may be a combination of an inner tube 10a and an outer tube 10b. The skirt 13 is formed in the inner tube 10a and the top portion 11 is formed in the outer tube 10b (FIGS. 8A to 8C). It is noted that FIGS. 8A to 8C are a central vertical sectional view, a top plan view and a front elevational view, respectively.

The outer tube 10b made of a soft material is integrally assembled with the inner tube 10a, as fitted over the inner tube 10a made of a hard material. A rib 16a for prevention of slip off is formed on an outside surface of an upper part of the inner tube 10a. An engaging groove 16b corresponding to the rib 16a is formed in the outer tube 10b. The orifices 12a, 12a . . . at the lower ends of the liquid-medicine passages 12, 12 . . . in the outer tube 10b are communicated with an upper end of an upward taper hole 15 formed in a center of the inner tube 10a. A bottom of the taper hole 15 opens into a ceiling of the skirt 13 via an upward orifice 15a. The liquid-medicine passages 12, 12 . . . are each formed modified-oblong-shaped in section having a longitudinal axis along a circumferential direction of the top portion 11.

The skirt 13 of the inner tube 10a together with a cover portion 14d under the outer flange 14b of the outer tube 10b are pressed into the opening 21 of the container 20. When the inner plug 10 is inserted into the opening 21, the cover portion 14d is elastically deformed to come into water-tight intimate contact with an inside surface of the opening 21 and with an outside surface of the inner tube 10a.

Similarly to the inner plugs 10 shown in FIGS. 1A and 1B and in FIGS. 5A and 5B, the inner plug 10 shown in FIGS. 8A to 8C is capable of applying the liquid medicine W (not shown) in the container 20 in a droplet. When the container 20 is returned to the upright position, the inner plug 10 makes the liquid medicine W adherent to the outside surface of the top portion 11 flow back into the container 20 even more smoothly via the orifices 12a, 12a . . . of the liquid-medicine passages 12, 12 . . . , the taper hole 15 and the orifice 15a. This is because the taper hole 15 and the orifice 15a are each smoothly expanded toward the top side thereof, so as to be able to apply a downward force by the surface tension to the liquid medicine W therein. The inner tube 10a made of the hard material prevents the liquid medicine W in the container 20 from coming into contact with the outer tube 10b made of the soft material, whereby the deterioration of the liquid medicine W is avoided.

Fourth Preferred Embodiment

Figure 9B:
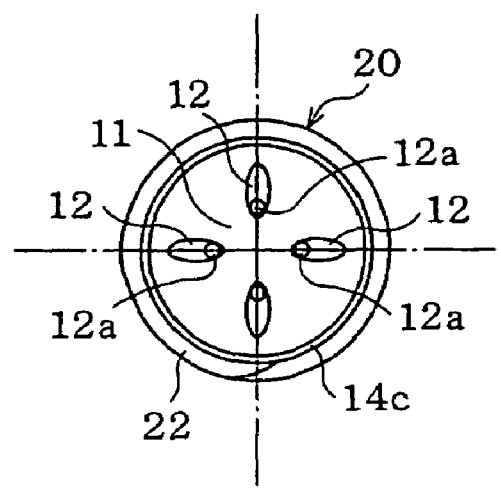
FIG. 9B is a top plan view of the nozzle of the fourth embodiment.
Figure 9A:
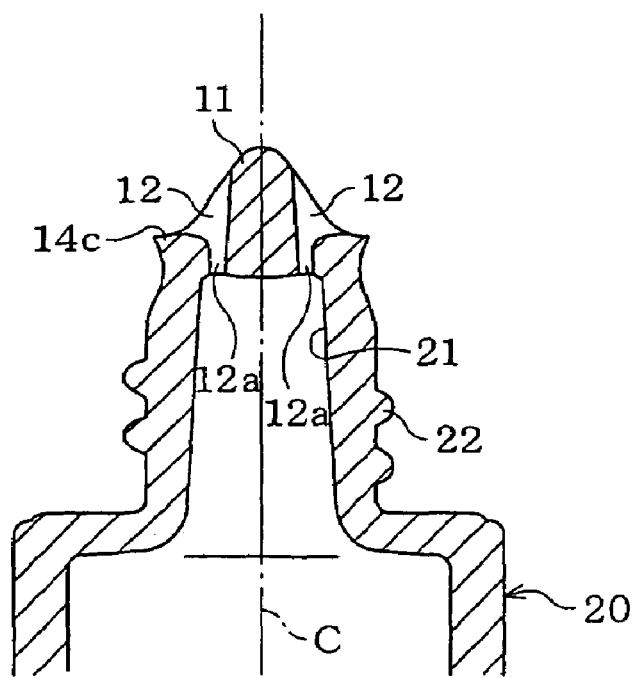
FIG. 9A is a vertical sectional view of a nozzle of a fourth embodiment.

The top portion 11 and the liquid-medicine passages 12, 12 . . . , shown in FIGS. 5A and 5B, along with the orifices 12a, 12a . . . and the edge 14c for draining may be formed in a single-piece form with the container 20 made of the hard material at the end of the opening 21 of the container 20 (FIGS. 9A and 9B). It is noted that FIGS. 9A and 9B are a central vertical sectional view and a top plan view, respectively.

Figure 10:
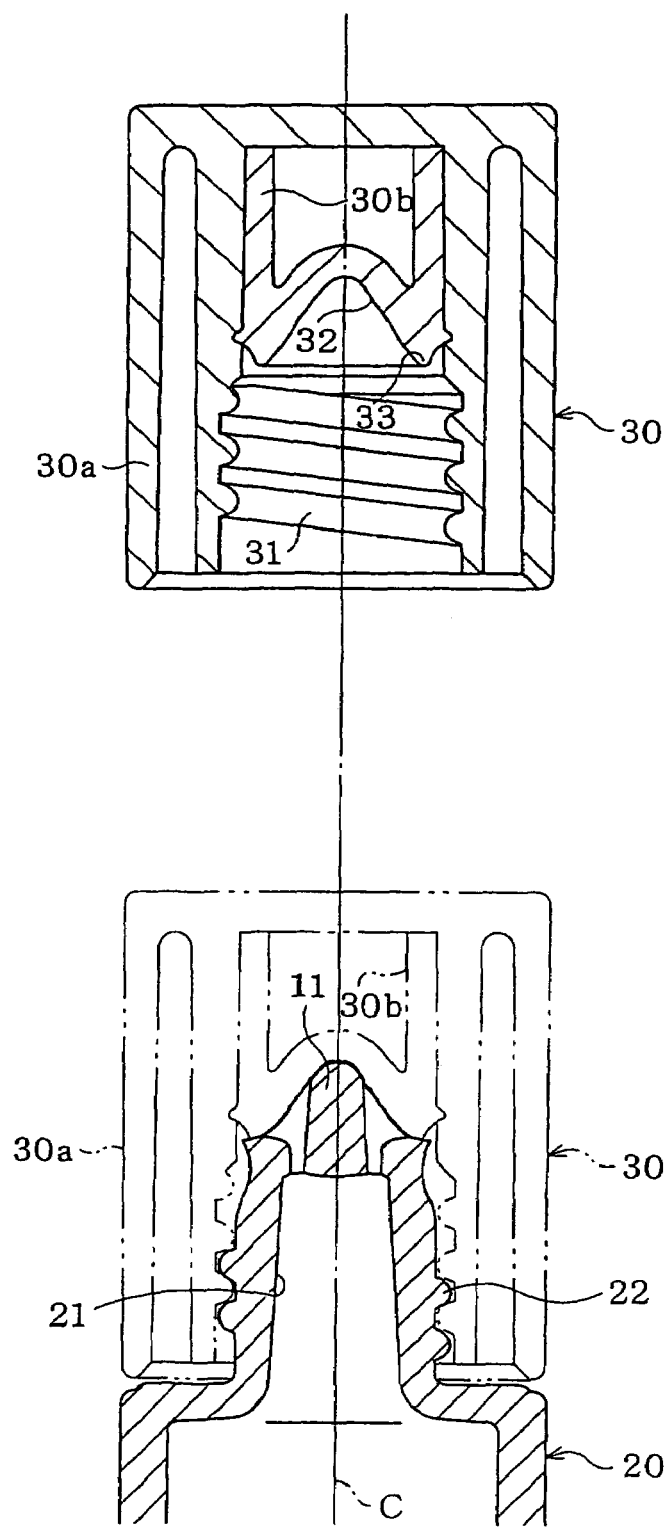
FIG. 10 is a vertical sectional view of a cap and the nozzle.

The cap 30 in this case is constructed by attaching a sealing member 30b to a ceiling of an outer cap 30b of a double tube formed in a single-piece form (depicted by the solid line in FIG. 10). It is noted that the female screw 31 matching with the male screw 22 on the container 20 is formed at an inner tube of the outer cap 30a, whereas the storage space 32 for storing the top portion 11 and the sealing portion 33 corresponding to the edge 14c are formed at a lower surface and at a lower edge of the sealing member 30b, respectively. When the container 20 and the outer cap 30a of the cap 30 are made of the hard materials, a soft material suited to the hard materials is selected for forming the sealing member 30b.

Figure 11A:
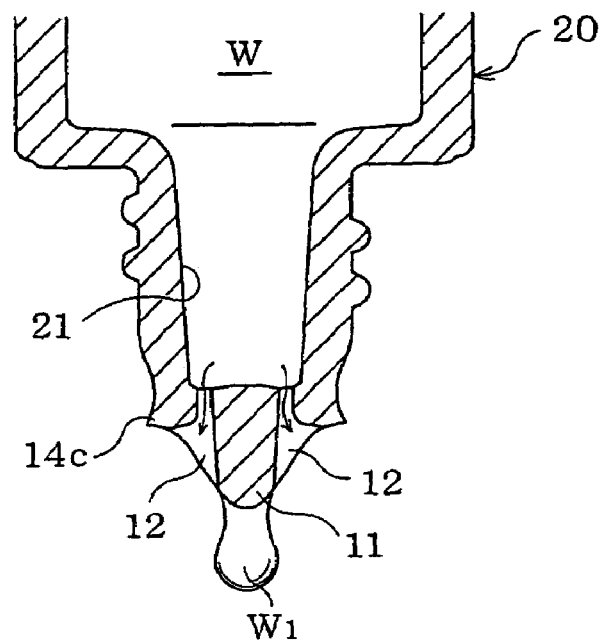
FIG. 11A is a vertical sectional view of a container directed downward.
Figure 11B:
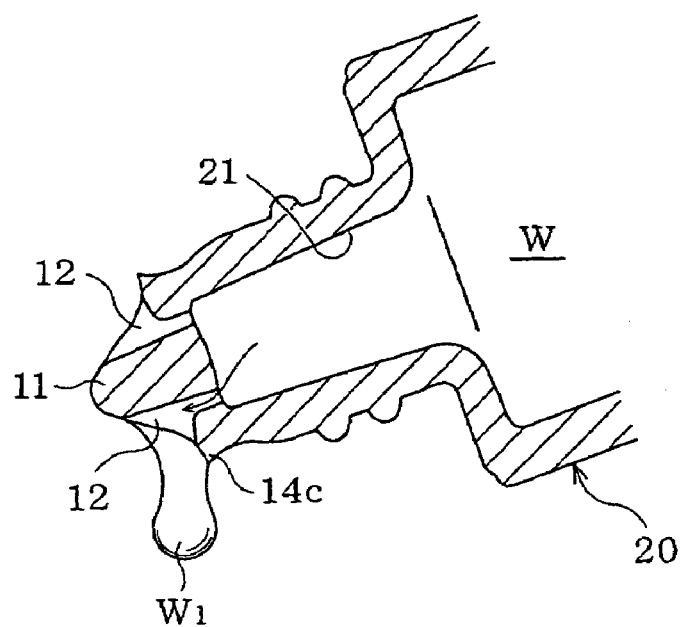
FIG. 11B is a vertical sectional view of the container inclined downward.

The cap 30 is capable of releasably sealing the opening 21 of the container 20 by means of the male screw 22 and the female screw 31 (depicted by the dash-double-dot line in FIG. 10). When the container 20 with the cap 30 removed therefrom is directed downward (FIG. 11A) or inclined at any angle (FIG. 11B), the liquid medicine W in the container 20 may be applied in a droplet W1 just the same way as in FIGS. 7A and 7B.

OTHER PREFERRED EMBODIMENTS

In the foregoing description, the top portion 11, the liquid-medicine passages 12, 12 . . . and the step 14a of the inner plug 10 shown in FIGS. 1A to 4B, may also be formed in a single-piece form with the container 20 at the end of the opening 21 of the container 20 after the examples shown in FIGS. 9A to 1B. In the foregoing embodiments, the liquid-medicine passages 12, 12 . . . formed at the outer periphery of the top portion 11 are not limited to the four passages shown in the figures but any plural number of passages may be arranged with equal spacing or at irregular space intervals. The sectional shape of each liquid medicine passage 12 may be a U-shape, an open-ended rectangular shape or the like instead of the V-shape or the oblong shape.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. A droplet nozzle for use in eye drop container, comprising:
    a top portion which is shaped like a dome, which projects in the same direction as an opening of said container, and which is provided with a plurality of liquid-medicine passages formed at an outer periphery thereof in a direction of an axis thereof;
    an intermediate portion which is molded integral with said top portion and formed at a foot thereof on the same axis thereof in a shape of a hollow cylinder; and
    a draining portion which is formed at a top of said intermediate portion and which is in a form of a step or an edge;
    wherein:
    the diameter of said draining portion is larger than the maximum outside diameter of said top portion, the maximum outside diameter of said top portion being the diameter at a lower end thereof;
    a plurality of orifices, which open at places closest to the axis of said top portion, are provided at lower ends of said plurality of liquid-medicine passages respectively, the cross-sectional area of each orifice being smaller than that of each liquid-medicine passage; and
    the lower end of each of said plurality of liquid-medicine passages is communicated with said opening of said container via each of said plurality of orifices and the interior of said intermediate portion.

2. The droplet nozzle for use in eye drop container as claimed in claim 1, wherein an inner plug is formed in a separate piece from said container, said inner plug including said top portion said intermediate portion and a skirt, said intermediate portion being provided with an outer flange at a lower end thereof, said skirt being pushed into said opening of said container, said outer flange conforming to an end face of said opening of said container.

3. The droplet nozzle for use in eye drop container as claimed in claim 2, wherein said inner plug is a combination of an inner tube which is made of a hard material and an outer tube which is made of a soft material and which is fitted over said inner tube, said inner tube being provided with a taper hole which extends in a direction of the axis, said skirt formed at a foot thereof, and said outer tube being provided with said top portion, said draining portion, and said outer flange, and wherein each of said plurality of liquid-medicine passages is communicated with said opening of said container via said orifice at the lower end of each liquid-medicine passage, said taper hole and an orifice formed in a center of said skin.

4. The droplet nozzle for use in eye drop container as claimed in claim 1, wherein said top portion, said draining portion, said plurality of liquid-medicine passages, said orifice at the lower end of each liquid-medicine passage are molded integral with said container at an end of said opening of said container.

* * * * *